United States Patent [19]
Mirza

[11] Patent Number: 5,816,246
[45] Date of Patent: Oct. 6, 1998

[54] ELECTRONIC POCKET SPIROMETER

[76] Inventor: M. Zubair Mirza, 570 Farview Ave., Wyckoff, N.J. 07481

[21] Appl. No.: 651,119

[22] Filed: May 21, 1996

Related U.S. Application Data

[63] Continuation of Ser. No. 306,476, Sep. 15, 1994.
[51] Int. Cl.⁶ .................................................... A61B 5/09
[52] U.S. Cl. .................... 128/726; 482/13; 73/861.76; 73/861.77
[58] Field of Search .................................. 128/725–727; 482/13; 73/861.15, 861.16, 861.17

[56] References Cited

U.S. PATENT DOCUMENTS

| | | |
|---|---|---|
| 3,946,726 | 3/1976 | Pikul . |
| 3,949,737 | 4/1976 | Nielson ................................. 128/726 |
| 4,122,842 | 10/1978 | Pikul . |
| 4,282,883 | 8/1981 | Yerushalmx ........................... 128/726 |
| 4,441,505 | 4/1984 | Edwards et al. ...................... 128/726 |
| 4,456,016 | 6/1984 | Nowacki et al. . |
| 4,469,194 | 9/1984 | McBride . |
| 4,509,511 | 4/1985 | Neufeld . |
| 4,546,793 | 10/1985 | Stupecky . |
| 4,638,812 | 1/1987 | Häkkinen . |
| 4,644,958 | 2/1987 | Brisson et al. . |
| 4,862,898 | 9/1989 | Hudimac, Jr. . |
| 4,989,456 | 2/1991 | Stupecky . |
| 4,995,400 | 2/1991 | Boehringer et al. .................. 128/725 |
| 5,033,312 | 7/1991 | Stupecky . |
| 5,038,621 | 8/1991 | Stupecky . |
| 5,038,773 | 8/1991 | Norlien et al. . |
| 5,058,601 | 10/1991 | Riker . |
| 5,060,655 | 10/1991 | Rudolph . |
| 5,137,026 | 8/1992 | Waterson et al. . |
| 5,277,195 | 1/1994 | Williams ................................. 482/13 |
| 5,413,112 | 5/1995 | Jansen et al. ......................... 128/726 |
| 5,549,117 | 8/1996 | Tacklind et al. ...................... 128/726 |
| 5,564,432 | 10/1996 | Thomson ............................... 128/725 |

FOREIGN PATENT DOCUMENTS

| | | | |
|---|---|---|---|
| 2560988 | 9/1985 | France | ................................. 128/726 |
| 2583283 | 12/1986 | France | ................................. 128/726 |
| 9319669 | 10/1993 | WIPO | ................................. 128/725 |

OTHER PUBLICATIONS

Vitalograph Safety Mouthpiece; Vitalograph, Inc. (1 page) (undated).
MultiSPIRO–SX/pc; MultiSPIRO Global Medical Innovation (2 pages) (undated).
Vitalograph Bacteriological Filter; Vitalograph, Inc. (1 page) (undated).
KoKo–Trek Spirometer; Pulmonary data Service Instrumentation, Inc. (2 pages) (undated).

(List continued on next page.)

*Primary Examiner*—Lee S. Cohen
*Attorney, Agent, or Firm*—Arnold, White & Durkee

[57] ABSTRACT

This invention relates generally to instrumentation for pulmonary monitoring and diagnosis and particularly to a compact, hand held, battery powered spirometer, measuring and monitoring expiratory and inspiratory flow rates, volumes and other lung function parameters.

An electronic "pocket" spirometer comprises an elongated handle having a mouth piece connected to a flow chamber mounted on one end thereof as an integral assembly. The flow chamber includes a centrally mounted pivotal vane which is restrained by a spring and driven by incoming breath to provide an output signal through an optical encoder to a microprocessor. The vane may move forward or backward providing expiratory as well as inspiratory flow/volume measurement. An optical wheel is locked in synch with the vane and moves correspondingly to activate the encoder which supplies flow rate and volume signals and other calculated parameters to an LCD display. The flow chamber is removable, washable and reusable which eliminates the need for a filter to prevent cross contamination with subsequent users as well as eliminates a variable and a possible source of error in measurement.

16 Claims, 7 Drawing Sheets

OTHER PUBLICATIONS

Pneumotach Special Bioburden Study (1 page), dated Mar. 20, 1989.

Spirolite Spirometers; Medical Systems International Corp. (1 page) (undated).

KoKo–Moe Filters; Pulmonary Data Service Instrumentation (1 page) (undated).

KoKo Filter; Pulmonary Data Service (3 pages) (undated).

Spirometrics Micro/MicroPlus Spirometer (1 page) (undated).

Spirometrics CMD PC Flow (1 page) (undated).

Puritan–Bennett; Single Patient Use Pneumotachs (2 pages) (undated).

Puritan–Bennett; Renaissance System (2 pages) (undated).

ELECTRONIC POCKET SPIROMETER

This application is a file wrapper continuation of application Ser. No. 08/306,476, filed Sep. 15, 1994.

BACKGROUND OF THE INVENTION

Devices used in the clinical environment called pulmonary function test equipment or spirometers, utilize a fair degree of sophistication and provide varying degrees of accuracy for diagnostic purposes. These spirometers utilize various means of electronic/computer technology to measure, flows, volumes, and even gas content of a breath. They compute, display, print and plot other parameters, compare with expected results, etc. and perform data management. As such, they range in price from approximately $1,000.00 to $40,000.00. They are generally based on various types of differential pressure transducers, Pneumotachometers, hot wire sensors, precision optical shaft or position encoders, etc.

Peak expiratory flow rate measuring and monitoring, using simple, low cost, portable mechanical devices has proven to be a good general indicator of the presence or absence of airway obstruction. It, therefore, serves as a reliable early indicator of a probable lung condition. Measuring with such devices is also useful in monitoring the degree of response to bronchiodilators, even when away from home or hospital. These single parameter devices cost approximately $20.00 to $25.00.

As patients have become more aware and educated about self-care, the utility of home health care devices also has increased. Peak flow is an important health indicator, but better care demands more and accurate information about the flow as well as the volume of expired and inspired air. Mechanical peak flowmeters are single parameter devices and are therefore, limited in their utility. This invention proposes a low cost, user friendly, multi-parameter spirometer which will not only fill the growing needs of patients, but will also be an indispensable screening, monitoring and perhaps, diagnostic tool for physicians, nurses and paramedics.

To date, all attempts to make a portable electronic spirometer have automatically reverted to using downsized versions of one of the more sophisticated techniques. Due to the nature of most of these techniques, they require air flow directly over the sensor or pressure sensing ports. A filter is, thus, required to prevent cross-contamination from patient to patient. Occasional and careful cleaning of the device is also necessary since minute amounts of dust and debris can often change the measurement and calibration. Frequent calibration of such devices is also a must. This results in either expensive devices, out of reach of most patients, or devices which are technically finicky or unreliable. Such devices cost in the range of $400.00–$1500.00.

This invention describes a simple, inexpensive ($30.00–$300.00, depending on features), portable electronic spirometer that primarily combines the simplicity of portable mechanical peak flowmeters with simple and rugged position detection electronics. The relative motion displacement of a mechanical vane or a piston, connected to a spring and riding inside a fixed space, against an incoming breath can be used to indicate its rate (flow) and amount (volume), using simple electronic computation.

Among the more relevant prior art patents are U.S. Pat. No. 4,638,812 to Hakkinen on an exhalation flow meter and U.S. Pat. No. 4,122,842 to Pikul on a pulmonary diagnostic instrument including breath transducer. Neither of the foregoing patents is believed to affect the patentability of the present invention but they are representative of the state of the art in the particular area.

Hakkinen discloses, for example, a means for measuring the peak flow of a person's exhalation wherein a flap having a pointer coupled thereto is moved by the breath flow against the urging of a spring. The flap and pointer rotate about at one end of the frame. The flap returns leaving the pointer indicating a reading on a printed scale. The only parameter that can thus be measured, as in all other similar devices, is peak expiratory air flow rate. The device, as all other mechanical peak flow meters, is primarily intended for single patient use. Multiple (single function, single parameter, limited use) use would require a bacterial filter.

Pikul discloses a flow tube in which a diaphragm is suspended for linear displacement when a person's breath passes directly through it. The diaphragm's displacement is measured with magnetic lines of flux. The device, although able to measure and calculate various parameters, is not economical and faced with all the problems of calibrations, and cross contamination, when used without a filter. The device is also quite finicky which is a considerable drawback.

SUMMARY OF THE INVENTION

This invention proposes a portable hand-held electronic spirometer. The spirometer comprises an elongated handle or body having a removable mouthpiece and flow chamber assembly mounted at one end. A user blows into the mouthpiece driving a rotatable piston or vane positioned in the middle of the flow chamber to register the movement via an optical wheel which is locked in synch at the axis with the spring loaded vane. The optical wheel incrementally counts steps and holds the time-stamped plotted curve in a scratch-pad (temporary) memory. Various expiratory and inspiratory flow parameters, such as PEFR, FEV1, FVC, FEF25–75, FEV/FVC, can thus be measured and/or calculated from the stored curve by a coupled microprocessor. Higher memory models may store the entire timed curve as flow-volume curve loop, for more extensive clinical research and diagnostic use and assessment.

Since the flow chamber is removable and rinse/washable, there is no need for a bacterial filter. Indeed several flow chambers can be provided for each spirometer for multiple patient use in a clinic or hospital. As a further advantage, positioning the vane in the middle of the chamber permits expiratory as well as inspiratory flow/volume measurements. However, in its simpler embodiment, positioning the vane closest to the mouthpiece would yield expiratory flow/volume measurements.

Separation of the breath from the sensor is one of the prime advantages of this invention. The flow chamber assembly is readily attached and detached from the main housing assembly. Other advantages include economy, accuracy,, and the ability to measure a full range of parameters with relatively simple electronics.

Accordingly, an object of this invention is to provide a new and improved compact hand held electronic spirometer to measure inspiratory and/or expiratory breath measurements.

Another object of this invention is to provide a new and improved portable spirometer having a removable and washable flow chamber to eliminate any chance of cross-contamination from patient to patient and thus also expanding its usability at minimal cost, while eliminating the cost inaccuracy of filters.

A further object of this invention is to provide a new and improved low cost, very affordable electronic spirometer with multi-parameter capability, to provide more functions that are more accurate and clinically more significant at a lower cost.

A more specific object of this invention is to provide a new and improved electronic spirometer with a reusable flow chamber which utilizes a rotatable or linearly moving spring-urged vane/piston which, in its preferred embodiment, works in cooperation with an optical wheel to supply a 4× resolution digital signal to a microprocessor for the measurement of various parameters such as rate of flow, volume, lung capacity, flow volume ratios, etc., in either an inspiratory and/or expiratory cycle. Other means and techniques may be employed such as Hall Effect Digital Vane Switch, low cost current, voltage, sonar, piezo, strain gauge or pressure sensors, etc. without altering or affecting the objects of the invention.

Yet another object of this invention is to provide an accurate yet simple and low cost device, through the use of sensitive but rugged, high resolution mass-produced sensing system and microprocessor components.

Another object of this invention is to provide a user friendly device that is simple in design and easy to use by the average patient, even in a vulnerable or poor condition of health.

A further object of this invention is to provide a spirometer that can reliably be used as a screening/diagnostic instrument by the health care provider.

Another object of this invention is to provide a very reliable monitoring spirometer for patients which is more accurate and broad in its functions than the state of the art, yet simpler to use.

Another object of this invention is to automate the data gathering functions, thus providing greater assurance, conformance of use, accuracy, reliability, functionality, ease of use and aiding in clinical assessment of the patient, while making it useful for the patient.

Yet another object of the invention is to provide and preserve the patient data and lung function history in a manner to assist the physician to accurately and quickly review the entire data, download to another computer, print/plot journals or reports, tabulate for research, etc., anywhere in the world, directly form the instrument, or through the use of plug-in credit card size data memory cards, readable on any PC for more accurate and effective diagnostic treatment.

A further object of this invention is to configure the various functions and mechanics of the device in a manner that greatly simplifies manufacturability, hence aiding reliability and cost.

Another object of this invention is to provide an interacting instrument between a health care provider and a patient in that the provider may set goals, targets and alarms for the patient, provide incentive for the patient to use and monitor his/her lung function/condition thereby aiding the health care provider in appropriately and efficiently diagnosing and treating the patient.

Yet another object of the invention is to provide a spirometer that can effectively be used as research instrument due to its accuracy, reliability and flexibility, thus, providing an instrument that is truly a multipurpose and multifunctional tool; from simple monitoring to diagnosis to research, with multiparameter data logger, and which is economical and easy to use, having rugged and reliable instrument capability.

As yet another object of this invention is to provide a self correcting, self calibrating, spirometer, since it resets itself from a base position before each measurement.

DESCRIPTION OF THE DRAWINGS

The above and other objects and advantage of the invention may be more clearly seen when viewed in conjunction with the accompanying drawings wherein:

FIG. 10 is a block diagram of the pocket spirometer.

DETAILED DESCRIPTION OF THE INVENTION

Referring now to the drawings, the invention comprises an electronic spirometer 10 having an elongated handle 11 with a display 12 and a key cluster 13a–13d for control and readout purposes. The keys denote power 13a, select 13b and scroll up 13c and scroll down 13d. A flow chamber 14 having an outwardly extending mouthpiece 15 is removably mounted to the upper portion of the handle at point 17. The chamber 14 snaps into a fixed location and is quickly removable by unlatching.

Figure 1:
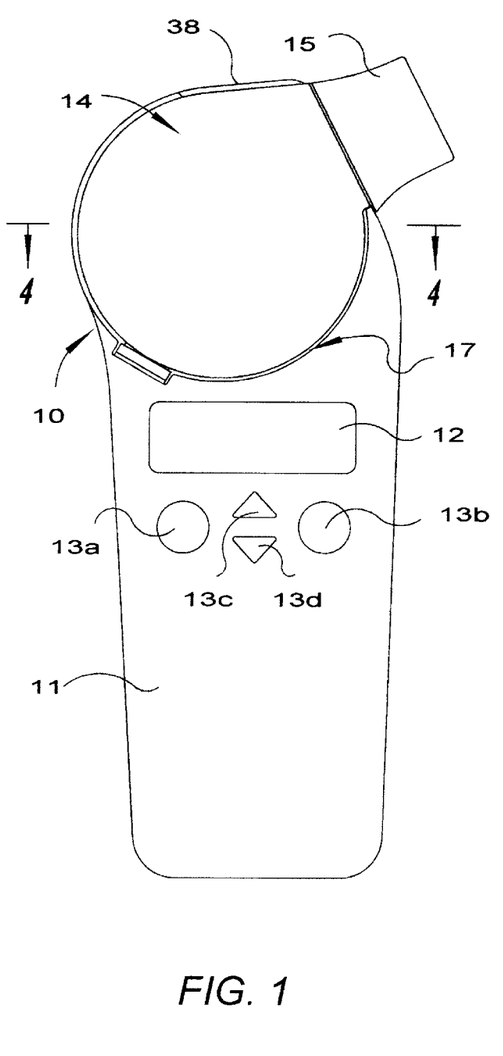
FIG. 1 is a front view of the portable/pocket electronic spirometer comprising the invention.
Figure 2:
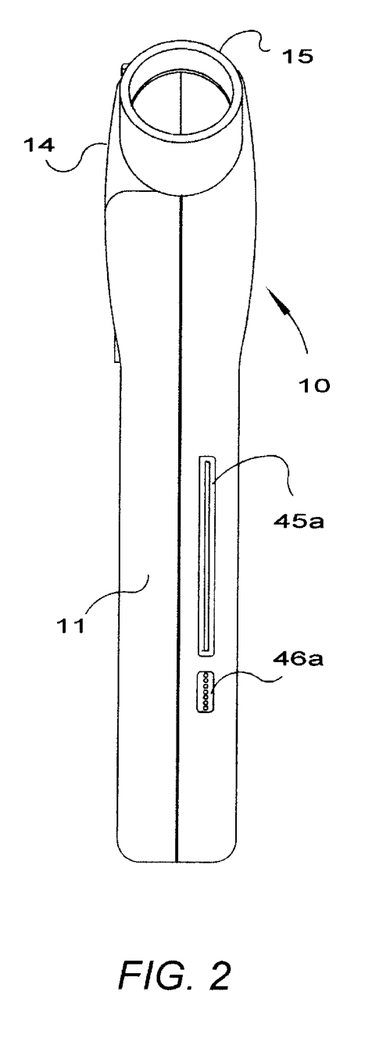
FIG. 2 is a side view of the invention illustrating the mouth piece in greater detail.
Figure 3:
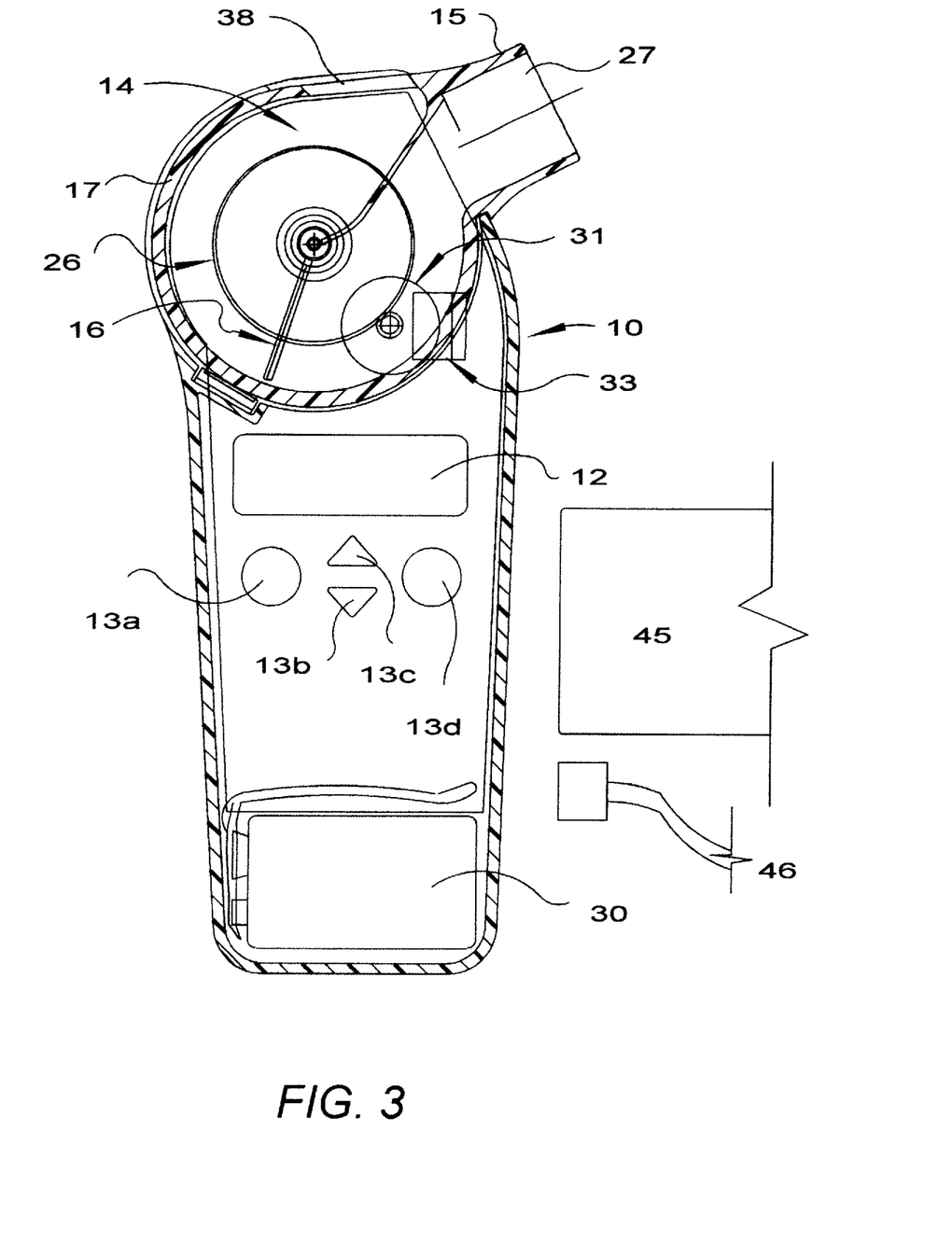
FIG. 3 is a front view with portions cutaway to illustrate the internal workings of the invention.
Figure 4:
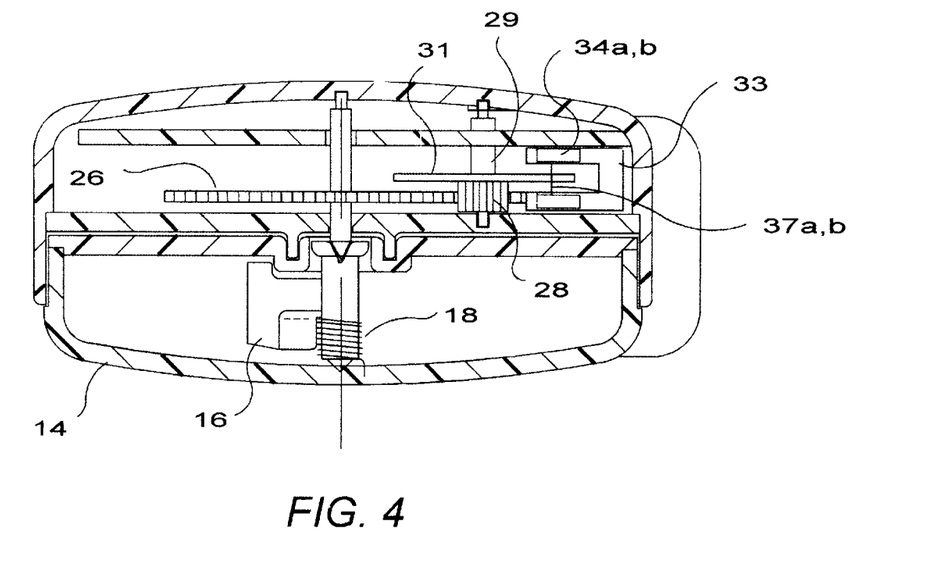
FIG. 4 is a view taken along the line A—A of FIG. 1.

A major feature of the invention is a disposable, reusable, removable and washable flow chamber 14 which eliminates the need for a filter to prevent cross contamination between subsequent users and eliminates an important variable. A vane 16 is mounted on pivot 19 and is urged in an initial position by spring 18 which is mounted about a cylinder portion 21 of the vane 16. The vane 16 comprises a cylindrical portion 21 at one end which engages the pivot 19 with its central aperture 22 and an outwardly extending blade 23 having a recess 24 adjacent to the lower portion of the cylinder 21. The spring 18 is mounted about the cylinder 21 and extends through the recess 24 to urge the vane 16 into an initial position. The vane 16 remains in this position as shown in FIG. 3 until use. Alternatively, the vane 16 may comprise a linearly movable piston which is driven by the incoming air.

A drive gear 26 is mounted about the elongated axial pivot 19 and is driven by the vane 16 when a user blows into the aperture 27 on the mouthpiece 15. The drive gear 26 engages a pinion gear 28 on shaft 29 which has an optical encoder wheel 31 mounted thereon. Gearing allows several portions of a simple optical wheel 31 or 51 with 8–20 openings 32 or bars 52. Thus minor displacement is magnified manyfold and then read at 4 times the resolution, with the quadrature optical encoder system 31 or 51, 34a, b and 36a,b to provide excellent accuracy. The drive gear 26 and pinion 28 may be driven by friction (rubberized surfaces) instead of gear toothed engagement. Alternatively, as shown in FIG. 5a–d the encoder wheel 31 can be eliminated and replaced by a large diameter, thin, clear, plastic disc 51 with silk screened black bars 52 to interrupt the light, especially for the exhalation only model to further reduce the cost. The flow chamber 14 could alternatively be in a linear configuration of a piston and cylinder, driving the encoder system through a rack and pinion gear arrangement.

An exhaust opening 38, located at the opposite end of the mouthpiece aperture 27, is of a varying or tapered configuration so as to allow maximum displacement of the vane 16 against the reducing flow/force of one's breath.

Figure 5:
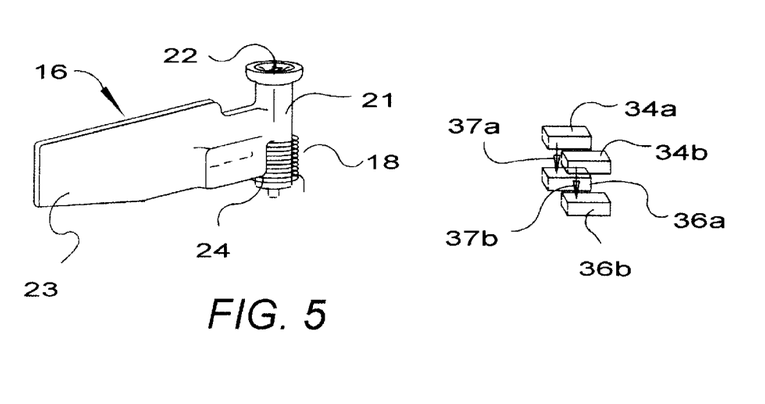
FIG. 5 and 5a–d illustrate the vane, the encoder wheel system and the operation thereof.
Figure 5A:
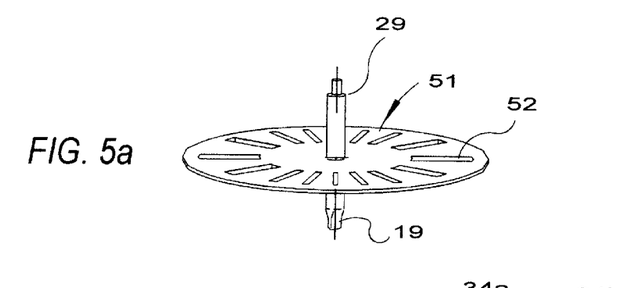
Figures 5B, 5C, 5D:
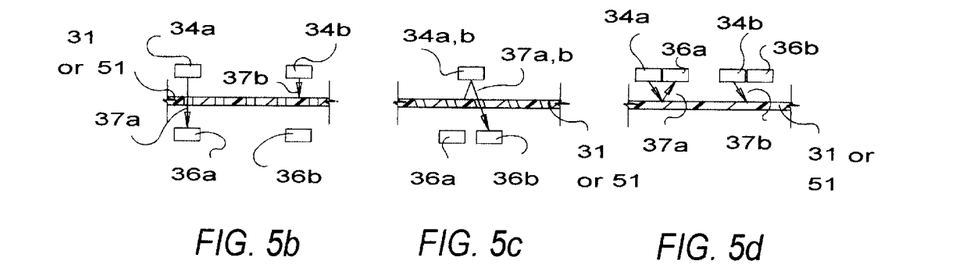
Figure 6:
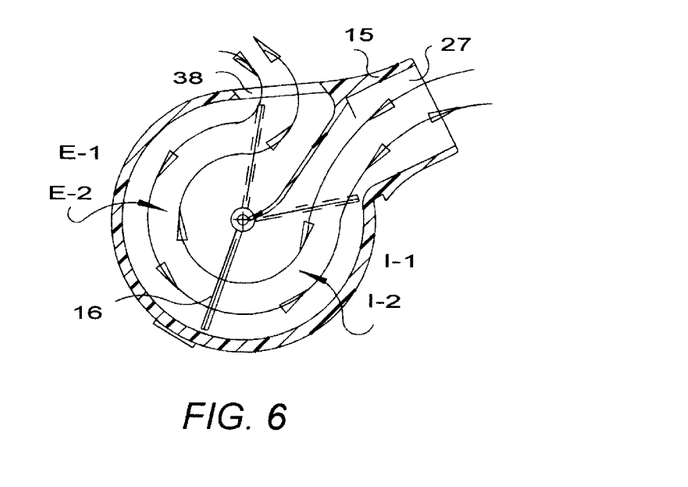
FIG. 6 is an internal view of the flow chamber showing the inspiratory and expiratory flow pattern and displacement inside the device.

The encoder wheel 31 or 51, as shown in FIG. 5 and 5a–d includes a plurality of spaced openings 32 or printed black bars 52 at spaced intervals. The wheel 31 or 51 rotates between the arms 35a and 35b of a substantially U-shaped member 33. Arm 35a includes a pair of light transmitting sources 34a and 34b and arm 35b includes a matching pair of receiving means 36a and 36b which receive light from the transmitters 34a, b as the light beams 37a, b are intermittedly cut by the rotating encoder wheel 31 or 51. Alternatively, light emitting and receiving diodes may both be located on the same side as shown in FIG. 5d and the beam 37 reflected off the bars printed on a white reflective surface of an optical wheel 31 or 51.

The receivers 36a, b transmit signals to a microprocessor 40 which plots the incoming signals and interprets the stored data for entry on the LCD display 12. The use of an incremental quadrature (paired) encoder system allows direction sensing as well as 4 times the resolution from a simple inexpensive optical wheel 31 or 51 and paired optocouplers 34a, b and 36a, b.

FIG. 10 is a block diagram showing the operation of the pocket spirometer 10. Accordingly, a patient blows into the mouthpiece 15 driving the flow chamber vane 16 which actuates the drive wheel 26 moving the encoder wheel 31 to provide a signal to the memory 41 which is then retrieved by the microprocessor 40. Power is provided to the system by the battery 30. The microprocessor 40 supplies measured and calculated values 42 to the LCD display 12. The results of the test can be stored in the patient memory 43. The scratch pad or temporary memory 41 can then be erased. The final test parameters can then be entered on memory cards 45 or in a personal computer 46.

At the completion of a test, the microprocessor 40 looks at the highest value reached on the expiratory flow curve and displays it as Peak Expiratory Flow Rate (PEFR) From the plot flow-time curve, Forced Expiratory Volume in one second (FEV1) can be easily calculated. Other parameters such as Forced Vital Capacity (FVC), Mid Expiratory Flow Rate, (FEF 25–75,) Forced Inspiratory Flow Rate (FIVC) at 50% (FIF 50), etc., can similarly be measured from the stored data.

Figure 7:
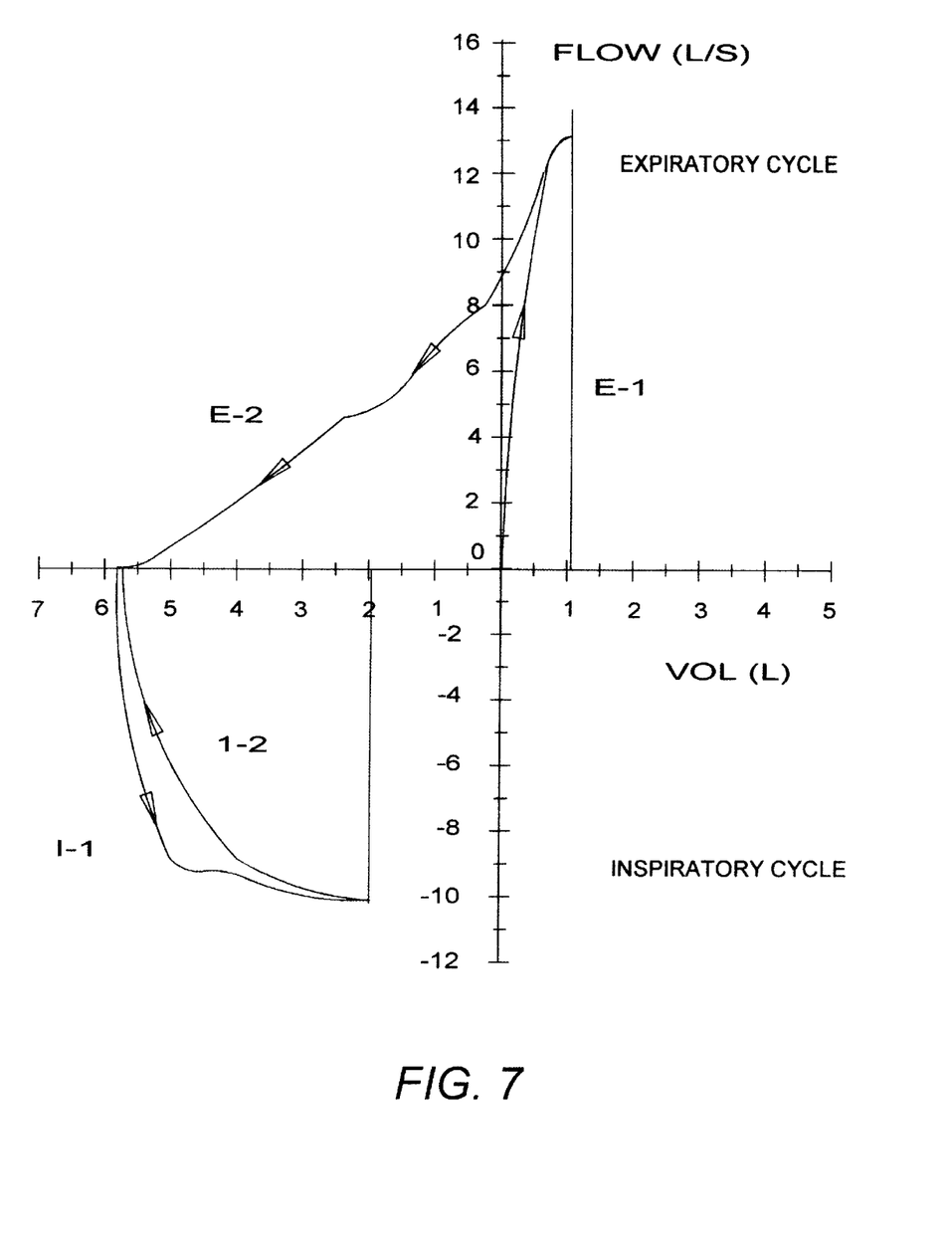
FIG. 7 is a representation of the flow-volume curve (loop) as it is tracked by the invention.
Figure 8:
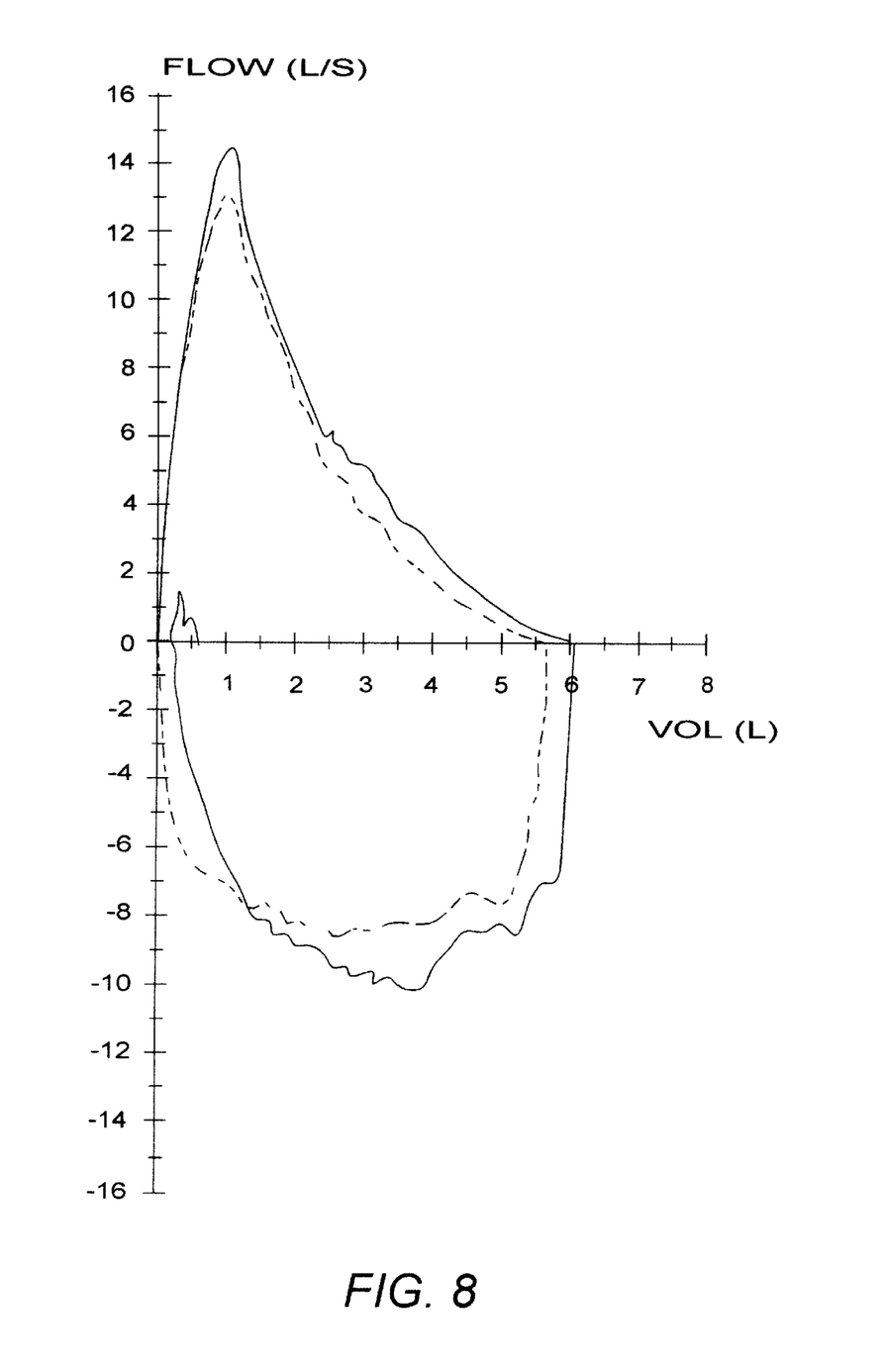
FIG. 8 is a typical flow volume loop (curve) for reference.
Figure 9:
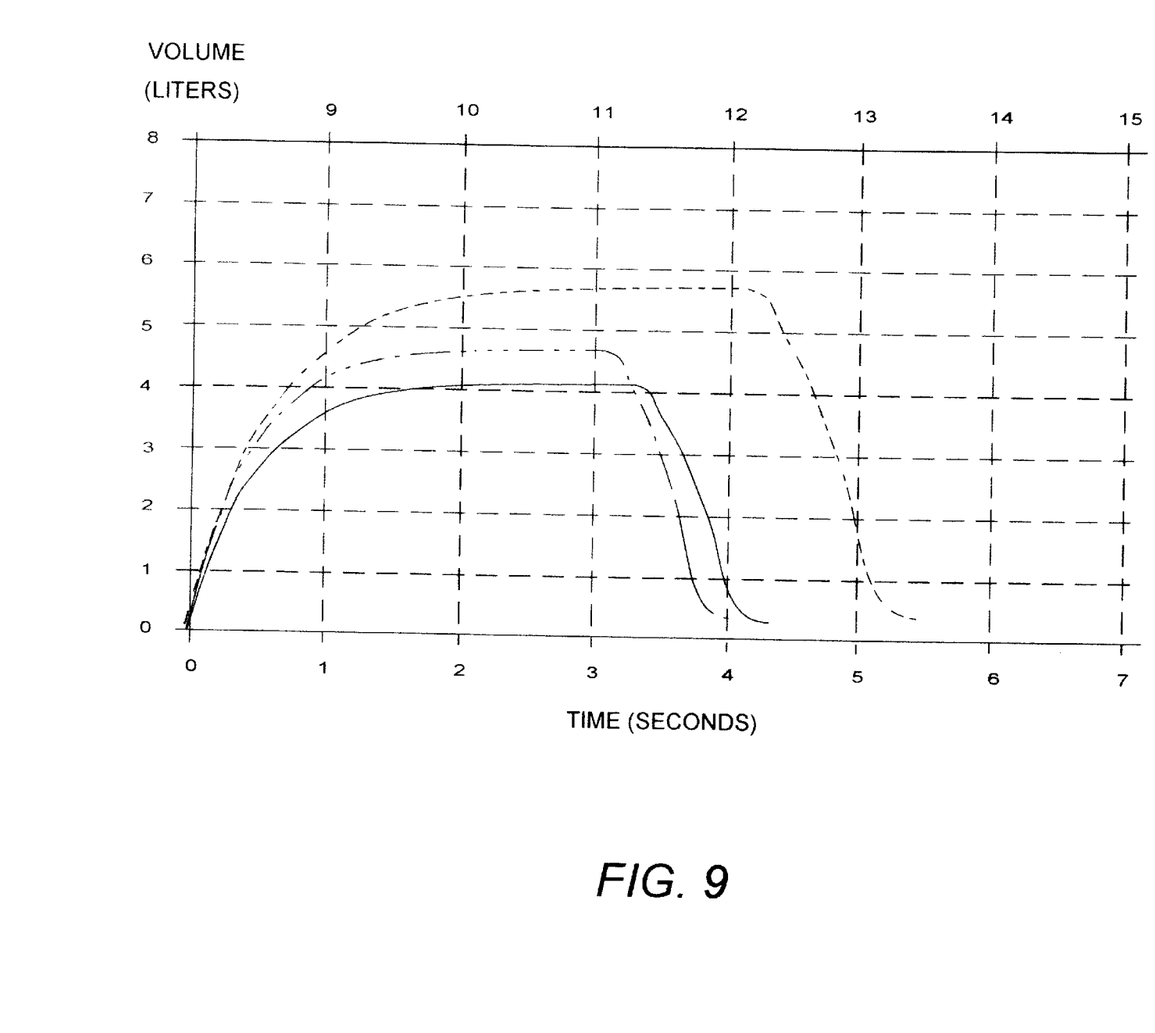
FIG. 9 is a typical volume time curve for reference.

FIG. 7 shows the expiratory and inspiratory cycles on a flow time chart while FIG. 8 shows a typical flow volume loop and FIG. 9 shows a volume-time curve. Once the basic parameters have been measured/calculated, the results can be compactly stored in the patient test memory. The memory hungry scratchpad memory of the flow-time curve can then be erased to make room for the next maneuver. Patient tests can be kept in a rolling memory always maintaining the last 50 to 100 tests, based upon the size of built-in memory. Higher memory models can store the entire timed curve as flow volume loop and volume time curve like a full-function diagnostic research clinical instrument. The data may alternatively or in addition, be stored on credit card size plug in memory cards for personalized patient data/history to store time/date-stamped event/recording, test, somewhat similar to Holter monitoring for cardiac patients. Data cards can then be mailed or given to the physician for assessment, storage, printing, plotting reports, etc. for more efficient diagnosis, monitoring and treatment decisions. Physicians may set goals, or targets using a computer (PC) or the key cluster 13a–13d. Date and time are automatically stamped on data for record and patient compliance. Best of three maneuvers and predicted values may also be a part of data collection and reference.

While the invention has been explained by a detailed description of certain specific embodiments, it is understood that various modifications and substitutions can be made in any of them within the scope of the appended claims which are intended also to include equivalents of such embodiments.

What is claimed is:

1. A system for determining body function parameters based upon the movement of human breath comprising:

a housing having an interior;

a flow chamber having walls forming an entry port for accepting the human breath, an exit port for exhausting the breath, and a fluid barrier between said flow chamber and the interior of said housing for preventing bacteria in said flow chamber from entering the interior of said housing, said flow chamber mounted to one end of said housing but being removable and detachable from said end of said housing;

sensing and measurement means for sensing the flow of human breath through said removable flow chamber and for producing a measurement of the flow of said human breath within said flow chamber, said sensing means includes a sensing element mounted in said flow chamber for movement in response to pressure from the user's breath exhaled into said entry port, and biasing means resisting movement of said sensing element, and said measurement means includes an encoder mounted outside said chamber and within said housing for producing a signal representing the movement of said sensing element as a function of time; and determination means for determining body function parameters based upon said signal.

2. The system of claim 1 wherein said measurement is in the form of an electrical signal.

3. The system of claim 1 wherein said sensing element comprises a pivotable vane driven by said human breath, and said biasing means is a spring restraining said vane.

4. The system of claim 1 further comprising a mouthpiece extending outwardly from said entry port of said flow chamber.

5. The system of claim 1 wherein said determination means comprise a microprocessor and memory storage device.

6. The system of claim 5 wherein said determination means calculates expiratory and inspiratory flow rates and volumes.

7. The system of claim 1 further comprising LCD display means for displaying the body function parameters calculated by said determination means.

8. The system of claim 1 further comprising computer means for customizing the display of said body function parameters.

9. A system for determining body function parameters based upon the movement of human breath comprising:

a housing having an interior;

a flow chamber having walls forming an entry port for accepting the human breath, an exit port for exhausting the breath, and a fluid barrier between said flow chamber and the interior of said housing for preventing bacteria in said flow chamber from entering the interior of said housing, said flow chamber mounted to one end of said housing but being removable and detachable from said end of said housing;

sensing and measurement means for sensing the flow of human breath through said removable flow chamber and for producing a measurement of the pressure of said human breath within said flow chamber, said sensing means includes a sensing element mounted in said flow chamber for movement in response to pressure from the user's breath exhaled into said entry port, and biasing means resisting movement of said sensing element, and said measurement means includes an encoder mounted outside said chamber and within said housing for producing a signal representing the movement of said sensing element as a function of time; and determination means for determining body function parameters based upon said signal.

10. The system of claim 9 wherein said measurement is in the form of an electrical signal.

11. A system for determining body function parameters based upon the movement of human breath comprising:

a housing having an interior;

a flow chamber having walls forming an entry port for accepting the human breath, an exit port for exhausting the breath, and a fluid barrier between said flow chamber and the interior of said housing for preventing bacteria in said flow chamber from entering the interior of said housing, said flow chamber mounted to one end of said housing but being removable and detachable from said end of said housing;

a vane mounted in said flow chamber for pivoting movement in response to the flow of said breath through said flow chamber by said human breath, a spring restraining said vane, and an encoding means mounted outside said chamber and within said housing for providing a signal representing the angular displacement of said vane in response to said human breath as a function of time;

processing means for calculating body function parameters using said signal; and display means for displaying said body function parameters.

12. The system of claim 11 wherein said signal is an electrical signal.

13. The system of claim 11 further comprising a mouthpiece extending outwardly from said entry port of said flow chamber.

14. The system of claim 11 wherein said processing means comprise a microprocessor and memory storage device.

15. The system of claim 11 wherein said display means is a LCD display and is mounted on said housing.

16. An electronic spirometer system for determining body function parameters based upon the movement of human breath comprising:

a housing;

a flow chamber having an entry port for accepting human breath and an exit port for exhausting the breath, said flow chamber mounted at one end of said housing but being removable and detachable from said end of said housing;

a mouthpiece extending outwardly from said entry port of said flow chamber;

a vane mounted in said flow chamber for pivoting movement in response to the flow of said breath through said flow chamber by said human breath, a spring restraining said vane, and an encoding means mounted outside said chamber and within said housing for providing a signal representing the angular displacement of said vane in response to said human breath as a function of time;

a microprocessor and memory storage device for calculating body function parameters using said signal;

an LCD display mounted on said housing for displaying said body function parameters; and computer means for customizing the display of said body function parameters.

* * * * *